US010604393B2

(12) United States Patent
Enoki et al.

(10) Patent No.: US 10,604,393 B2
(45) Date of Patent: Mar. 31, 2020

(54) PARTICLE SUCTION CAPTURE MECHANISM AND UNSTOPPING DEVICE EQUIPPED WITH PARTICLE SUCTION CAPTURE MECHANISM

(71) Applicant: Hitachi High-Technologies Corporation, Tokyo (JP)

(72) Inventors: Hideo Enoki, Tokyo (JP); Shigeki Yamaguchi, Tokyo (JP); Takahiro Sasaki, Tokyo (JP); Tooru Inaba, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 426 days.

(21) Appl. No.: 15/327,484

(22) PCT Filed: Jun. 29, 2015

(86) PCT No.: PCT/JP2015/068605
§ 371 (c)(1),
(2) Date: Jan. 19, 2017

(87) PCT Pub. No.: WO2016/031379
PCT Pub. Date: Mar. 3, 2016

(65) Prior Publication Data
US 2017/0166428 A1    Jun. 15, 2017

(30) Foreign Application Priority Data

Aug. 27, 2014    (JP) ................................ 2014-172171

(51) Int. Cl.
*B67B 7/00*        (2006.01)
*B08B 9/032*       (2006.01)
(Continued)

(52) U.S. Cl.
CPC ............ *B67B 7/00* (2013.01); *B01D 19/0094* (2013.01); *B08B 9/0327* (2013.01); *G01N 35/04* (2013.01);
(Continued)

(58) Field of Classification Search
CPC ........ B01D 45/16; B01D 45/12; B01D 45/00; B01D 19/0031; B01D 19/0042;
(Continued)

(56) References Cited

U.S. PATENT DOCUMENTS 4,390,351 A * 6/1983 Matsui ............... B01D 19/0057
                                                        210/512.1
5,314,529 A * 5/1994 Tilton ..................... B01D 45/16
                                                        96/204
(Continued)

FOREIGN PATENT DOCUMENTS

CN          102225278 A     10/2011
DE    10 2005 030 615 A1    2/2007
(Continued)

OTHER PUBLICATIONS

International Search Report PCT/JP2015/068605 dated Oct. 6, 2015.
(Continued)

*Primary Examiner* — Sameh Tawfik
*Assistant Examiner* — Valentin Neacsu
(74) *Attorney, Agent, or Firm* — Mattingly & Malur, PC

(57) ABSTRACT

A device for unstopping a stopped specimen vessel that contains a liquid specimen such as blood is equipped with a mechanism which sucks and captures particles floating around the opening of the specimen vessel and prevents contamination of the specimen. The unstopping device grips a vessel and the stopper of the opening of the vessel, and removes the stopper from the opening of the vessel by
(Continued)

changing the relative distance between the vessel-gripping mechanism and the unstopping mechanism. The unstopping device is equipped with: suction holes for sucking therethrough the gas which is present around the opening and contains liquid or solid particles; a pipeline which is connected to the suction holes and through which the sucked gas and particles are led downstream; a suction device connected to the pipeline; and a spirally flexed pipeline part disposed between the pipeline and the suction device.

9 Claims, 9 Drawing Sheets

(51) Int. Cl.
*G01N 35/04* (2006.01)
*B01D 19/00* (2006.01)
*B01L 3/00* (2006.01)
*B01L 1/04* (2006.01)
*B67B 7/02* (2006.01)
*B65B 31/00* (2006.01)

(52) U.S. Cl.
CPC ...... *B01D 19/0031* (2013.01); *B01D 19/0042* (2013.01); *B01L 1/04* (2013.01); *B01L 3/50825* (2013.01); *B65B 31/00* (2013.01); *B67B 7/02* (2013.01)

(58) Field of Classification Search
CPC ............ B01D 19/0047; B01D 19/0073; B01D 19/0094; B01L 3/50825; B01L 3/56; B04C 2009/004; B04C 2009/005; B04C 2009/007; F01N 3/037; G01N 35/04; B67B 7/00; B67B 7/02; B65B 31/00; B65B 55/24
USPC ............... 210/512.1, 512.2, 512.3; 55/459.3, 55/459.4, 461; 53/167, 381.4, 510; 96/188–192, 204, 208, 214, 219
See application file for complete search history.

(56) References Cited

U.S. PATENT DOCUMENTS

| | | | | |
|---|---|---|---|---|
| 5,460,147 A | * | 10/1995 | Bohl | B01D 45/12 123/572 |
| 5,647,906 A | | 7/1997 | Monday et al. | |
| 6,125,841 A | | 10/2000 | Boudreault | |
| 8,012,248 B2 | * | 9/2011 | Yun | B01D 45/14 96/244 |
| 9,168,473 B2 | * | 10/2015 | MacGregor | B29C 31/042 |
| 9,242,196 B2 | * | 1/2016 | Abayev | B04C 1/00 |
| 2003/0100125 A1 | * | 5/2003 | Pressman | B01D 61/18 436/177 |
| 2008/0250933 A1 | * | 10/2008 | Yun | B01D 45/14 96/251 |
| 2008/0276758 A1 | | 11/2008 | Itoh | |
| 2012/0031275 A1 | * | 2/2012 | Yun | B01D 45/14 96/309 |
| 2014/0212344 A1 | * | 7/2014 | Nagaoka | G01N 35/04 422/547 |
| 2014/0238239 A1 | * | 8/2014 | Abayev | B04C 1/00 95/271 |
| 2015/0037695 A1 | * | 2/2015 | Ward | H01M 8/20 429/409 |
| 2015/0151229 A1 | * | 6/2015 | MacGregor | B29C 31/042 425/145 |

FOREIGN PATENT DOCUMENTS

| | | |
|---|---|---|
| JP | 03-226485 A | 10/1991 |
| JP | 08-201364 A | 8/1996 |
| JP | 2008-279128 A | 11/2008 |
| JP | 2014-001926 A | 1/2014 |
| JP | 2014-1926 A | 1/2014 |
| JP | 2014001926 A * | 1/2014 |
| WO | 2007/028987 A2 | 3/2007 |

OTHER PUBLICATIONS

Chinese Office Action in corresponding Chinese Application No. 201580034905.3 dated May 24, 2018.
Extended European Search Report in corresponding European Application No. 15835374.8 dated Mar. 22, 2018.

* cited by examiner

PARTICLE SUCTION CAPTURE MECHANISM AND UNSTOPPING DEVICE EQUIPPED WITH PARTICLE SUCTION CAPTURE MECHANISM

TECHNICAL FIELD

The present invention relates to an apparatus for uncapping a capped sample container, the uncapping device including a mechanism for preventing contamination from sample to sample by sucking and capturing an airborne material in the air.

BACKGROUND ART

As a background art of the present technical field, there is an uncapping device including a mechanism for sucking and capturing a particle of JP 2014-1926 A (PTL 1). The uncapping device described in PTL 1 includes partition plates for covering the circumference of a sample container transferred, container gripping mechanisms that fix the sample container in a pinching manner and has an air intake function for sucking air around the sample container by means of power of an exhaust fan connected via a pipe, and an uncapping mechanism having a discharge function that removes a cap attached to the sample container and discharges air by means of power of a discharge fan connected to the circumference of the sample container via a pipe. With this apparatus, an airborne material, e.g., mist, is sucked to the container gripping mechanisms by an airflow generated between the uncapping mechanism and the container gripping mechanisms so that a micro-level airborne material, e.g., dirt and mist floating in the atmosphere, do not enter the uncapped sample container. Furthermore, the exhaust fan includes a filter on the suction side so that an airborne material, e.g., sucked mist, is not discharged through the exhaust fan.

CITATION LIST

Patent Literature

PTL 1: JP 2014-1926 A

SUMMARY OF INVENTION

Technical Problem

In PTL 1, the filter provided on the suction side of the exhaust fan is a cloth one that covers the inlet of the fan. However, because a filter of a type embedded in a cartridge is also commercially available, one conceivable way would be to attach the filter in the middle of the pipe. Such filters remove mist in the air or entered dust by filtering the air with a filter member includes porous flow passages in a micrometer order. However, as time elapses, each flow passage is blocked and the fluid resistance is gradually increased so that the air intake rate is gradually reduced. As the air intake rate is reduced, the airborne material is not fully sucked, resulting in a reduction in removal capability.

Generally, it is said that a filter is replaced at the time when the fluid resistance is doubled. In that case, the air intake rate in the case where the filter is new must be twice or more the rate required for suction of mist, resulting in an increase in size of the fan. Furthermore, in order to know the time for replacement, accessories, e.g., a pressure gauge, are required. Thus, there is a possibility that the size of the apparatus is increased or the costs regarding components and electricity are increased. Furthermore, it is difficult to clean and regenerate the porous flow passages during maintenance in terms of technique, cost, and fouling. Furthermore, in the case of replacement, dried mist or dust is dispersed from the filter member during disassembly and fouls the environment. Thus, there is a possibility that contamination is increased.

The present invention provides an uncapping device including a particle suction capture mechanism that is small in size, low in cost, allows easy maintenance, and has less contamination from sample to sample.

Solution to Problem

In order to solve the aforementioned problem, for example, a configuration is adopted in which an uncapping device with container gripping mechanisms for gripping a container and an uncapping mechanism for gripping a cap of an opening of the container and removes the cap from the opening of the container by changing a relative distance between the container gripping mechanisms and the uncapping mechanism, and the uncapping device includes a suction hole which is present around the opening and sucks gas containing a particle formed of liquid or solid, a pipe which is connected to the suction hole and introduces the sucked gas and particle downstream, a suction device connected to the pipe, and a helically curved pipe portion arranged between the pipe and the suction device.

Advantageous Effects of Invention

According to the present invention, an airborne material floating around the container can be removed from the environment of the opening and the removed airborne material is prevented from fouling the air intake device, eliminating the need of cleaning maintenance for the air intake device.

DESCRIPTION OF EMBODIMENTS

In the following, examples of the present invention are described in conjunction with the drawings.

Example 1

Example 1 of the present invention is described in conjunction with FIGS. 1 to 7.

Figure 1:
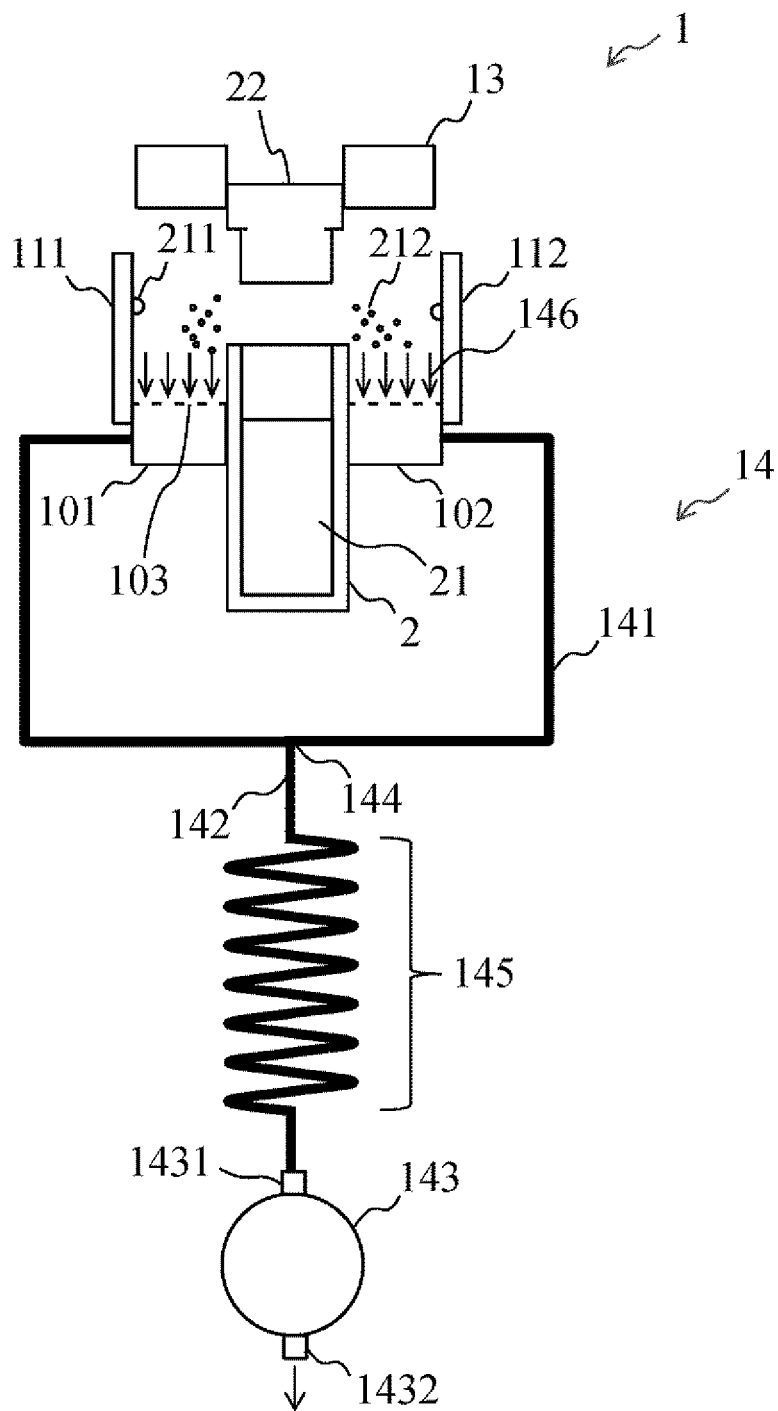
FIG. 1 is a configurational view of an uncapping device of a first example.

FIG. 1 is a configurational view of an uncapping device 1. The uncapping device 1 includes a pair of container gripping mechanisms 101, 102 configured to perform left and right air suction functions and which have a pair of partition plates 111, 112 attached to the container gripping mechanisms 101, 102, respectively, and an uncapping mechanism 13. The uncapping device 1 further includes an air intake system 14 comprised of a pipe 141 both ends of which are connected to the container gripping mechanisms 101, 102, respectively, a pipe 142 branched from a branch portion 144 in the vicinity of the middle of the pipe 141, and an air intake device 143, e.g., a pump or a fan, having an air intake port 1431, which is connected to the pipe 142, and a discharge port 1432 for discharging sucked air.

Generally, the pipe is formed to be straight and circular in cross-section. However, the present example includes a coil portion 145, which is formed as the pipe 142 is partially deformed and is turned in a helical fashion. The coil portion may be formed by preliminarily working a metal pipe or plastic tube into a helical shape. However, a flexible one, e.g., a plastic tube, may be wound and fixed onto a hard cylindrical surface, e.g., of a pipe. Furthermore, a transparent tube may be used. Furthermore, fine irregularities may be formed on the inner wall by processing, e.g., sandblasting. Furthermore, the inner wall may be coated with a surface treatment agent that changes the wettability, provides adhesiveness, or prevents growth of fungi or bacteria. The coil portion may be formed on parts of the pipe 141 near the container gripping mechanisms 101, 102 with respect to the branch portion 144. Furthermore, a pair of air intake systems may be used in which a pipe with a coil portion and an air intake device are connected to each of the container gripping mechanisms 101, 102.

Figure 2:
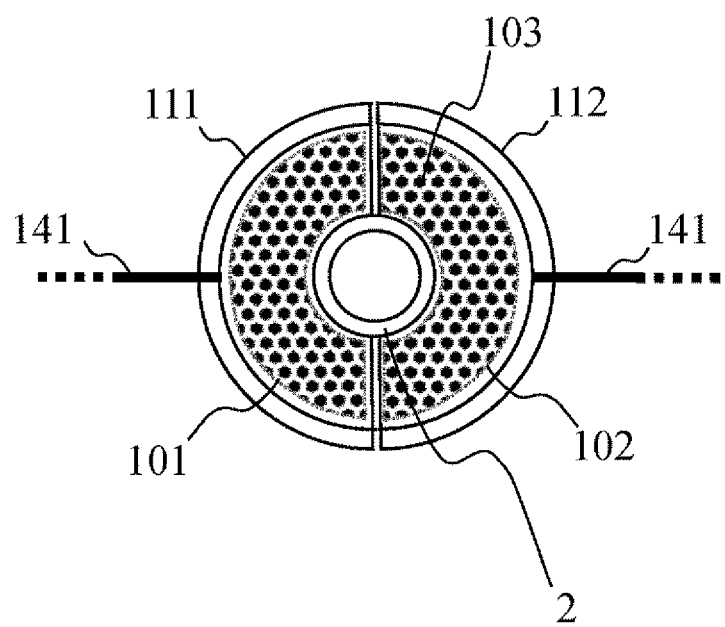
FIG. 2 is a top view of container gripping mechanisms of the uncapping device of the first example.

FIG. 2 is a top view of the container gripping mechanisms 101, 102 and the partition plates 111, 112 attached to the container gripping mechanisms 101, 102, respectively. The container gripping mechanisms 101, 102 and the partition plates 111, 112 have a shape of a cylinder that has been cut along the cylindrical axis. The pair of container gripping mechanisms 101, 102 are opened and closed right and left by a power source, e.g., a motor, and a power transmission mechanism, e.g., a link mechanism, according to a command from a control device, which is not illustrated. Thus, the pair of container gripping mechanisms 101, 102 grip and fix a columnar sample container 2, e.g., a test tube, which stores a sample solution 21, by means of the cylindrical inner surfaces of the container gripping mechanisms 101, 102.

A great number of holes 103 of the same shape are uniformly arranged through upper surfaces of the container gripping mechanisms 101, 102, and the insides are hollow. The air intake system 14 of the container gripping mechanisms 101, 102 sucks air through the holes 103 as the air intake device 143 is operated according to a command of the control device, which is not illustrated. Since the great number of holes 103 of the same shape are uniformly arranged through the upper surfaces of the container gripping mechanisms 101, 102, airflows generated by the suction are homogenized. Furthermore, the pair of partition plates 111, 112 are attached along the cylindrical outer surfaces of the container gripping mechanisms 101, 102 so as to surround the circumference of the side surface of the sample container 2 when the container gripping mechanisms 101, 102 are closed.

FIG. 1 illustrates a state immediately after the cap 22, which had been attached to the sample container 2, has been uncapped by being gripped and lifted with the uncapping mechanism 13 that is operated by a power source, e.g., a motor, and a power transmission mechanism, e.g., a link mechanism, according to a command from the control device, which is not illustrated, with the sample container 2 being pinched and fixed by the pair of container gripping mechanisms 101, 102. When part of the sample solution 21 is adhered to the inner side of the cap 22 or the sample container 2 during conveyance of the sample container 2, there is a possibility that the part of the sample solution 21 is spread into a liquid film as the sample container 2 and the cap 22 are separated by uncapping, and the liquid film is broken, atomized, and dispersed. Furthermore, it is also conceivable that an airborne material floating in the atmosphere enters the inside of the sample container 2 through the opening made after uncapping. Relatively large airborne droplets 211 and the airborne material floating at a distance from the sample container 2 impinge on and are captured by the partition plates 111, 112 that cylindrically cover the circumference of the sample container 2. The airborne material floating near the sample container 2 and relatively small airborne droplets (mist 212) floating around the sample container 2 are sucked into the holes 103 by airflows 146, which are generated as the air intake system 14 is activated, and are moved in the pipe toward the air intake device 143.

The mist 212 sucked into the air intake system 14 flows in the pipe 141 parallel to the pipe wall. However, when passing through the coil portion 145 having a helical shape, the mist 212 helically revolves in the coil portion 145, is moved outward perpendicularly to the helical axis by means of a centrifugal force, and impinges on the pipe wall. The mist 212, which has impinged on the pipe wall, is captured on the pipe wall of the coil portion 145. Thus, the mist 212 does not foul the air intake device 143, which is arranged downstream of the coil portion 145. The air intake device 143 is prevented from being fouled, eliminating the need of cleaning maintenance of the air intake device 143.

According to the present example, a part of the pipe is deformed into a coil shape, and the mist 212 can be captured, eliminating the need of a filter, thereby enabling a reduction in size and cost of the apparatus. Furthermore, regarding cleaning of the pipe, it is sufficient that the pipe 142 including the coil portion 145 is detached, soaked in disinfectant or detergent, and is subject to flushing. Therefore, maintenance is made easier.

Furthermore, because the mist 212 is captured on the inner wall of the coil portion 145 in the middle of the pipe 142, the captured mist 212 is isolated from both ends of the pipe 142 during replacement. Thus, there is no chance of external contact, enabling prevention of contamination without fouling the environment. Furthermore, when the coil portion 145 is formed of a transparent member, e.g., a plastic tube, the status of capture of the mist 212 inside can be observed contactlessly and directly by means of visual checking or an optical sensor or the like. Thus, maintenance can be performed reliably and efficiently. Furthermore, when fine irregularities are formed on the inner wall of the coil portion 145, the mist 212 is prevented from being separated after being closely attached to the inner wall and dried. Thus, the dried mist is hardly separated to foul the suction device 143, enabling prevention of contamination. Furthermore, when a surface treatment agent that changes the wettability of the inner wall of the coil portion 145 or provides adhesiveness is applied, the mist 212 is closely attached to the inner wall and dust and dirt generated by the separation of the dried mist can be again adhered and fixed to the inside of the coil portion. Therefore, fouling of the apparatus is suppressed and contamination is prevented. Furthermore, when the inner wall of the coil portion 145 is coated with a surface treatment agent that prevents growth of fungi or bacteria, the generation of dust and dirt, e.g., spores, is suppressed and contamination can be prevented.

Figure 3:
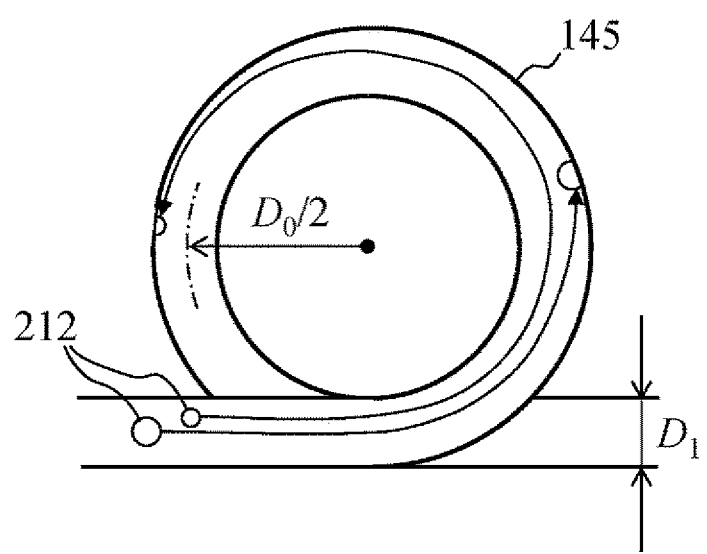
FIG. 3 is a detailed view of a coil portion of the first example.

FIG. 3 is a view illustrating the shape of the coil portion 145. The mist 212, which has reached the coil portion 145 together with air, flows along the flow of airflows while revolving in a helical fashion. At this time, the mist 212 is subject to a centrifugal force pointing outward perpendicularly to the central axis of the coil portion 145. Thus, the mist 212 moves in the coil portion 145, and reliably impinges on and is captured on the wall surface as it moves outward.

As an example, a coil portion 145 is considered. The coil portion 145 is formed as a pipe 142 having a diameter D1 is turned about the central axis into a loop having a diameter D0. FIG. 3 expresses one turn for the sake of simplicity. However, in practice, the loop is turned multiple times. Here, D0>>D1, and a centrifugal force acting on the mist 212 in the coil portion 145 is constant. When a direction perpendicular to the cylindrical surface including the loop is defined as r coordinate, a motion equation composed of an inertia force, a viscous force (air resistance) and a centrifugal force acting on the mist 212 is represented by Formula 1 when the weight of the mist 212 is represented by m, the diameter is represented by d, the density is represented by $\rho$, the viscosity of air is represented by $\mu$, and the angular velocity around the cylindrical surface is represented by $\omega$.

[Math. 1]

$$m\ddot{r} + 3\pi\mu d\dot{r} - \frac{mD_0\omega^2}{2} = 0 \qquad \text{[Formula 1]}$$

When the mist 212 is small, the first term of Formula 1 is negligible. When time is represented by t and integration is performed with respect to time, Formula 2 is obtained.

[Math. 2]

$$r = \frac{\rho D_0 d^2 \omega^2}{36\mu}t + r_0 \qquad \text{[Formula 2]}$$

Incidentally $r_0$ is the initial position of the mist 212. Furthermore, air flow velocity $v_a$ in the coil portion 145 can be regarded as $D_0\omega/2$. Therefore, Formula 2 can be rewritten into Formula 3.

[Math. 3]

$$r = \frac{\rho d^2 v_a^2}{9\mu D_0}t + r_0 \qquad \text{[Formula 3]}$$

When the flow rate is represented by Q, the entire length of the coil portion 145 is represented by L, and mixing is assumed to be absent in the coil portion 145, all the mist 212 reaches the wall surface of the coil portion 145 as the mist moves across the diameter of the coil portion 145 at most after entering the coil portion 145, i.e., as the movement distance from the initial position $r-r_0$ becomes equal to $D_1$. Thus, the length $L_a$ of the coil portion 145 required for capturing all the mist 212 is given by Formula 4.

[Math. 4]

$$L_a = \frac{9\pi\mu D_0 D_1^3}{4\rho d^2 Q} \qquad \text{[Formula 4]}$$

Next, the capability of the coil portion 145 for capturing the mist 212 was assessed through an experiment, and the validity of Formula 4 was examined.

Figure 4:
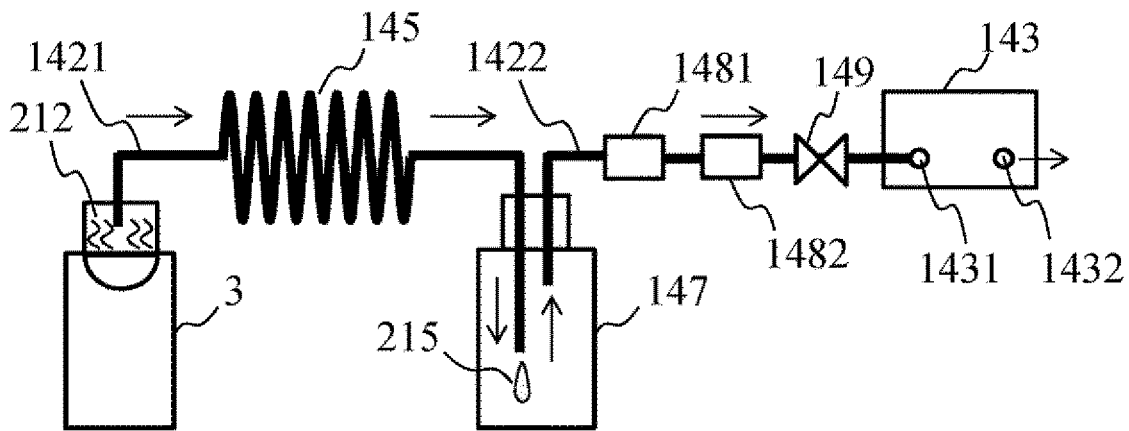
FIG. 4 is a configurational view of a mist capture assessment system of the first example.

FIG. 4 illustrates a mist capture capability assessment system. An ultrasonic medical nebulizer 3 was used to simulate the generation of mist. The mist 212 generated by the nebulizer 3 has a particle size of 1 to 8 µm and moves in line with the flow of air in cloudlike clusters.

The coil portion 145 is arranged in the middle of a pipe 1421 one end of which is inserted into a mist generation port of the nebulizer 3. The other end of the pipe 1421 on the downstream side is connected to the interior of a sealed recovery bottle 147. Furthermore, a pipe 1422 one end of which is inserted into the recovery bottle 147 is provided with a flow rate sensor 1481 and a temperature and humidity sensor 1482, and is connected to the air intake port 1431 of the air intake device 143 via a control valve 149. The amount of mist generated by the nebulizer 3 is about 1.5 mL/min. The mist 212 is layered and accumulated on the inner wall of the coil and is formed into a droplet, which is swept away by an airflow. The airflow from the coil portion 145 is temporarily released into the recovery bottle 147. Therefore, a droplet 215 generated in the coil portion is recovered in the recovery bottle 147, and the airflow free of a droplet flows toward the air intake device 143. The air flow rate is adjusted as the opening of the control valve 149 is changed.

Figure 5:
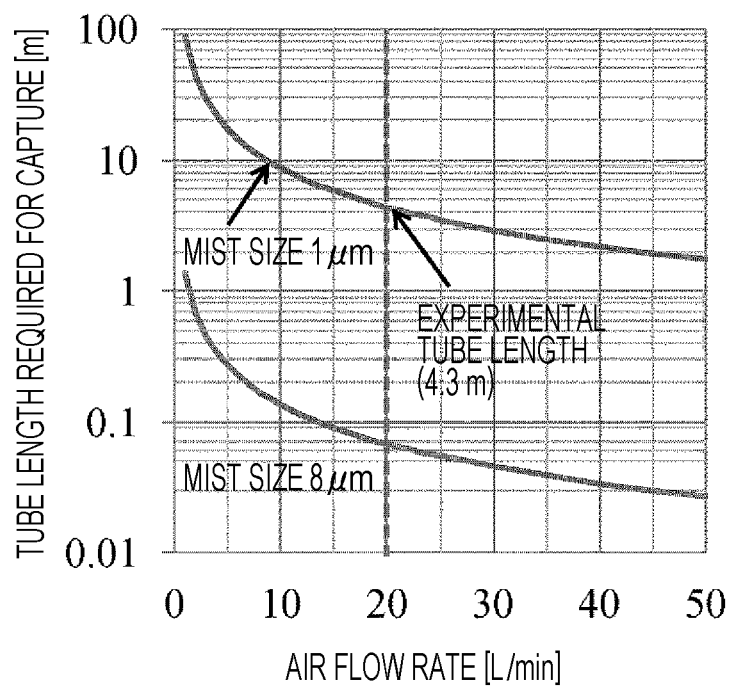
FIG. 5 is a diagram indicating the length of a coil portion required for mist capture of the first example.

The shape of the coil portion 145 used in the present experiment has an inside diameter of 6 mm, an outside diameter of 8 mm, a length of 4.3 m, and a loop diameter of 60 mm. However, the shape of the coil portion is not limited to the present shape. FIG. 5 indicates the length of the coil portion 145 required for capturing the mist, which is estimated by Formula 4, according to a change of the air flow rate with respect to the coil portion 145 having an inside diameter of 6 mm and a loop diameter of 60 mm. When the smallest size of the mist generated from the nebulizer 3 is 1 µm, it is estimated that about 4.3 m suffices as the length of the coil portion 145 required for capturing the mist 212 when the air flow rate is 20 L/min or more.

Figure 6:
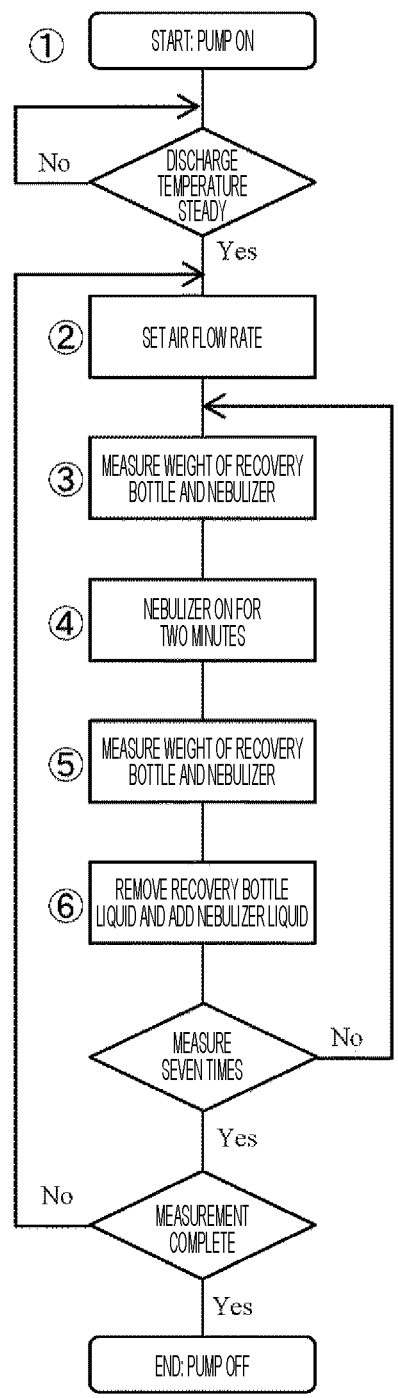
FIG. 6 is a diagram indicating an experimental flow of the first example.

FIG. 6 indicates the flow of a verification experiment.

Step 1: The operation is continued until the discharge temperature is stabilized in a state where the nebulizer 3 is stopped and the mist 212 is not generated.

Step 2: The opening of the control valve 149 is adjusted to set an air flow rate.

Step 3: The weights of the recovery bottle and the nebulizer are measured.

Step 4: The nebulizer is driven for two minutes.

Step 5: The weights of the recovery bottle and the nebulizer are measured again.

Step 6: The liquid recovered in the recovery bottle is removed, and liquid is added to the nebulizer.

Step 7: The procedure from Steps 3 to 6 is repeated seven times, and a data set under one flow rate condition is obtained.

The amount of increase in weight of the recovery bottle 147 and the amount of reduction in weight of the nebulizer 3 before and after the nebulizer 3 is driven in Step 4 are calculated from a difference between the weights obtained in Steps 3 and 5. Thus, the capture amount of the mist captured by the coil portion 145 and the amount of the mist introduced into the coil portion 145 are determined. While the mist 212 generated moves in the pipe, the water is likely to evaporate. Therefore, during experiment, the temperature and humidity of the air flowing in the pipe is continuously measured with the temperature and humidity sensor 1482, and the amount of evaporation is calculated in combination with the temperature and humidity of outdoor air.

The amount of mist=the weight of nebulizer measured in Step 3–the weight of nebulizer measured in Step 5

The amount of capture=the weight of recovery bottle measured in Step 5–the weight of recovery bottle measured in Step 3 The amount of evaporation=air flow rate×mist generation time×(the amount of water vapor in pipe–the amount of water vapor in outdoor air)

The amount of water vapor a is calculated on the basis of the Tetens formula indicated in Formula 5.

[Math. 5]

$$\begin{cases} e = 6.11 \times 10^{\frac{7.5T}{T+237.3}} \\ a = \frac{217eR_H}{100(T+273.15)} \end{cases}$$ [Formula 5]

Here, in Formula 5, T: temperature [° C.], e: saturation water vapor pressure [hPa], RH: relative humidity [%], a: the amount of water vapor [g/m$^3$].

Figure 7:
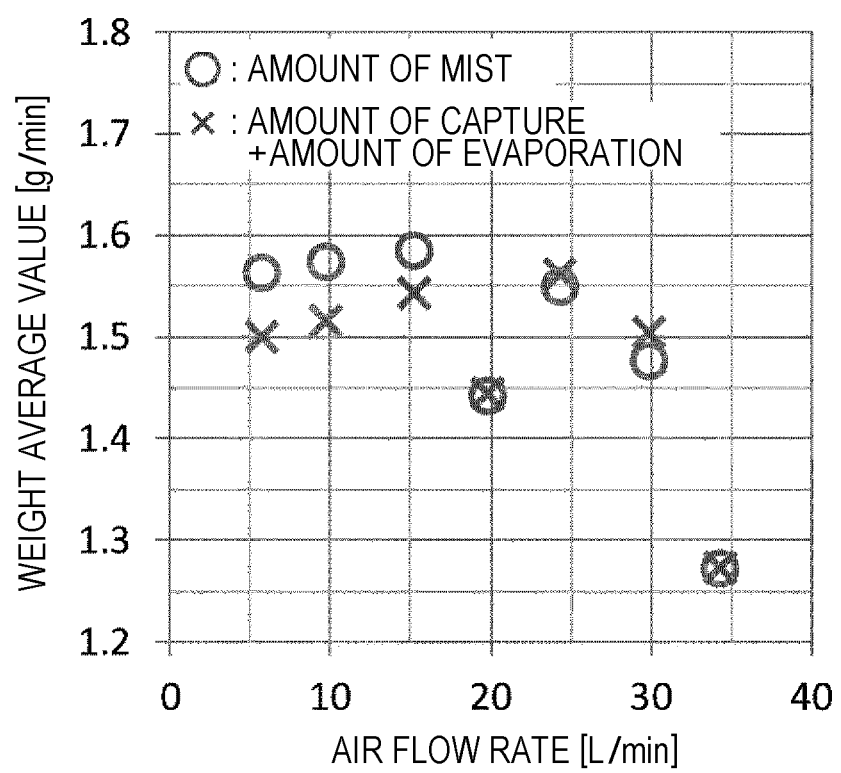
FIG. 7 is a diagram of the amount of mist and the amount of capture+the amount of evaporation according to a change of an air flow rate of the first example.

FIG. 7 illustrates a graph plotting the amount of mist (o), and the sum of the amount of capture and the amount of evaporation (x) according to a change of the air flow rate. Each data is an average value of five out of seven experiment trials excluding the largest value and the smallest value. When the air flow rate is smaller than 20 L/min, the amount of mist is greater by about three to four percent than the sum of the amount of capture and the amount of evaporation. This indicates that part of the mist 212 generated by the nebulizer 3 has flown downstream of the recovery bottle 147, i.e., part of the mist 212 has not been captured but has flown out to the air intake device 143. It is indicated that, when the air flow rate is 20 L/min or more, the amount of mist almost corresponds to the sum of the amount of capture and the amount of evaporation, and almost all the mist generated by the nebulizer 3 has been captured by the coil portion 145. According to the above experimental results, it can be confirmed that the mist can be captured 100% when the air flow rate is 20 L/min or more. This corresponds to the value estimated in Formula 4, and the validity of Formula 4 was verified.

The present example has the following effect. When a target mist size or intake flow rate is given, the shape of the coil portion 145 can be arbitrarily designed according to Formula 4. Therefore, the mist 212 can be recovered reliably, and the reliability of the apparatus is increased. Furthermore, because the length of the coil portion 145 can be set to the minimum, the apparatus can be reduced in size and cost. Furthermore, because the capture capability of the coil portion 145 can be assessed by the mist capture assessment system, inspection and quality assurance of the capture mechanism are made possible, increasing the reliability of the product.

Furthermore, only when a part of the pipe is deformed into a coil shape, the mist can be captured. Therefore, the need of a filter is eliminated, enabling a reduction in size and cost of the apparatus. Furthermore, regarding cleaning of the pipe, it is sufficient that the pipe including the coil portion is detached, soaked in disinfectant or detergent, and is subject to flushing. Therefore, maintenance is made easier. Furthermore, because the mist is captured on the inner wall of the coil portion arranged in the middle of the pipe, the captured mist is isolated from both ends of the pipe during replacement. Thus, there is no chance of external contact, enabling prevention of contamination without fouling the environment.

Furthermore, when the coil portion is formed of a transparent member, e.g., a plastic tube, the internal capture status can be observed contactlessly and directly by means of visual checking or an optical sensor or the like. Thus, maintenance can be performed reliably and efficiently.

Furthermore, when fine irregularities are formed on the inner wall of the coil portion, the mist is prevented from being separated after being closely attached to the inner wall and dried. Thus, the apparatus is not fouled by the separation, enabling prevention of contamination. Furthermore, when the inner wall of the coil portion is coated with a surface treatment agent that changes the wettability of the inner wall or provides adhesiveness, the mist is closely attached to the inner wall and dust and dirt separated after being dried is again adhered and fixed to the inside of the coil portion. Therefore, fouling of the apparatus is suppressed and contamination can be prevented. Furthermore, when a coating of a surface treatment agent that prevents growth of fungi or bacteria is applied, the generation of dust and dirt, e.g., spores, is suppressed and contamination can be prevented.

Example 2

Figure 8:
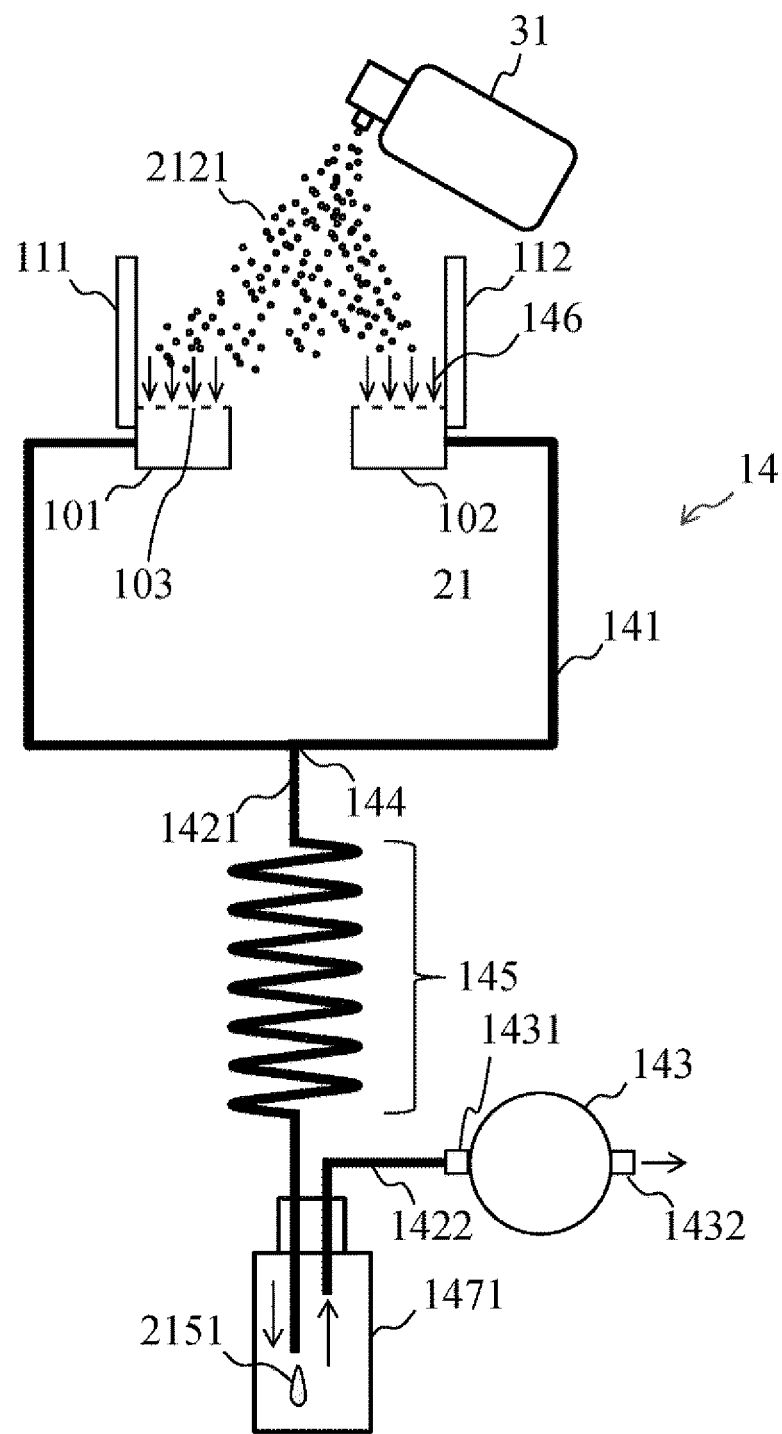
FIG. 8 is a view illustrating a method of cleaning a coil portion of a second example.

As Example 2 of the present invention, decontamination or maintenance of the particle suction capture mechanism is described. FIG. 8 is a view illustrating a state in which maintenance of cleaning the interior of the coil portion 145 is being carried out.

The other end of the pipe 1421 including the coil portion 145 on the downstream side is opened into a sealed, waste liquid collection equipment 1471. Furthermore, the pipe 1422 one end of which is inserted into the waste liquid collection equipment 1471 is connected to the air intake port 1431 of the air intake device 143. The waste liquid collection equipment 1471 recovers a droplet. The waste liquid collection equipment 1471 may be the recovery bottle 147 indicated in Example 1 or a cyclone. Furthermore, the connection of the air intake device 143 may be released and an air intake device for maintenance may be connected.

During maintenance, the air intake device 143 is activated, and then cleaning mist 2121 obtained as cleaning liquid is atomized by a cleaning mist source 31, e.g., a spray or a nebulizer, is fed to the great number of holes 103, which are present through the upper surfaces of the container gripping mechanisms 101, 102. The size of the cleaning mist 2121 is equal to or more than the smallest size that can be recovered by the coil portion. The cleaning mist 2121 passes through the holes 103, and reaches and is captured by the coil portion 145. Then, the cleaning mist 2121 contacts and dissolves in the mist 212, which has been captured on the inner wall of the coil portion 145, and is formed into a waste droplet 2151. The waste droplet 2151 is stored in the waste liquid collection equipment 1471 on the downstream side and does not flow to the air intake device 143. The waste liquid collection equipment 1471 and the pipe 1422 may be attached during maintenance or may always be mounted on the air intake system 14. Furthermore, the coil portion 145 and the waste liquid collection equipment 1471 may be formed of transparent material, e.g., plastic or glass.

The present example has the following effect. Without removing the particle suction capture mechanism, the suction function of the particle suction capture mechanism may be used to suck the cleaning mist 2121 and cleans the interior of the pipe. Therefore, maintenance is made easier and contamination due to fouling of the environment during disassembly can be prevented. Furthermore, because the cleaning liquid is turned into mist, the mist is similarly adhered to a portion where the mist of the sample solution has been accumulated, enabling an increase in cleaning efficiency and a reduction in amount of cleaning liquid.

Example 3

Figure 9:
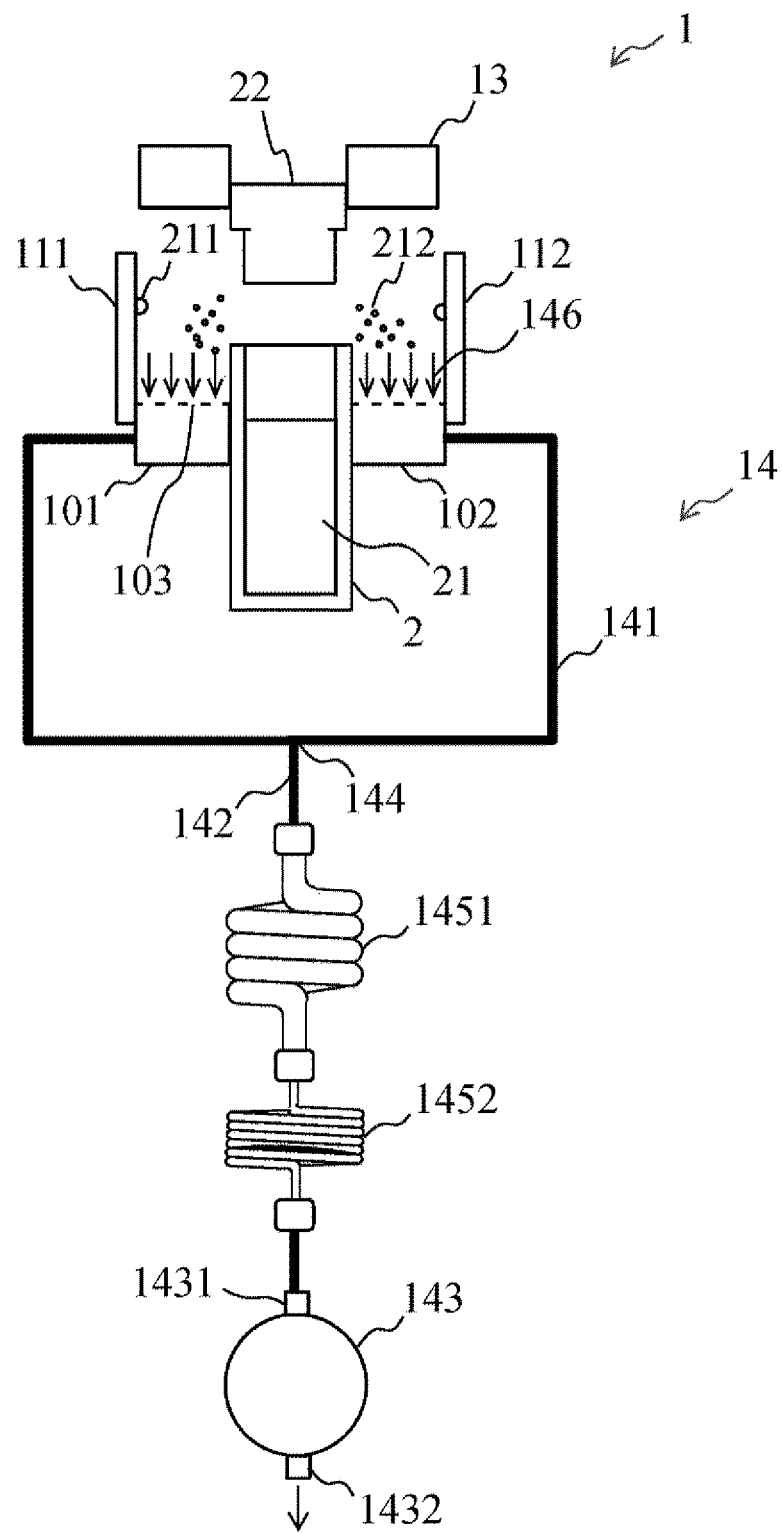
FIG. 9 is a configurational view of a coil portion of a third example.
Figure 10:
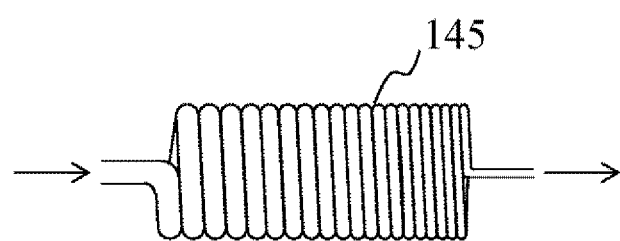
FIG. 10 is a view illustrating the shape of a coil portion of a fourth example.
Figure 11:
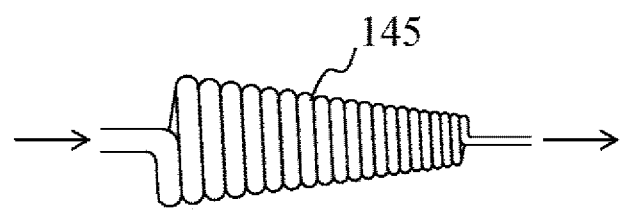
FIG. 11 is a view illustrating the shape of a coil portion of a fifth example.
Figure 12:
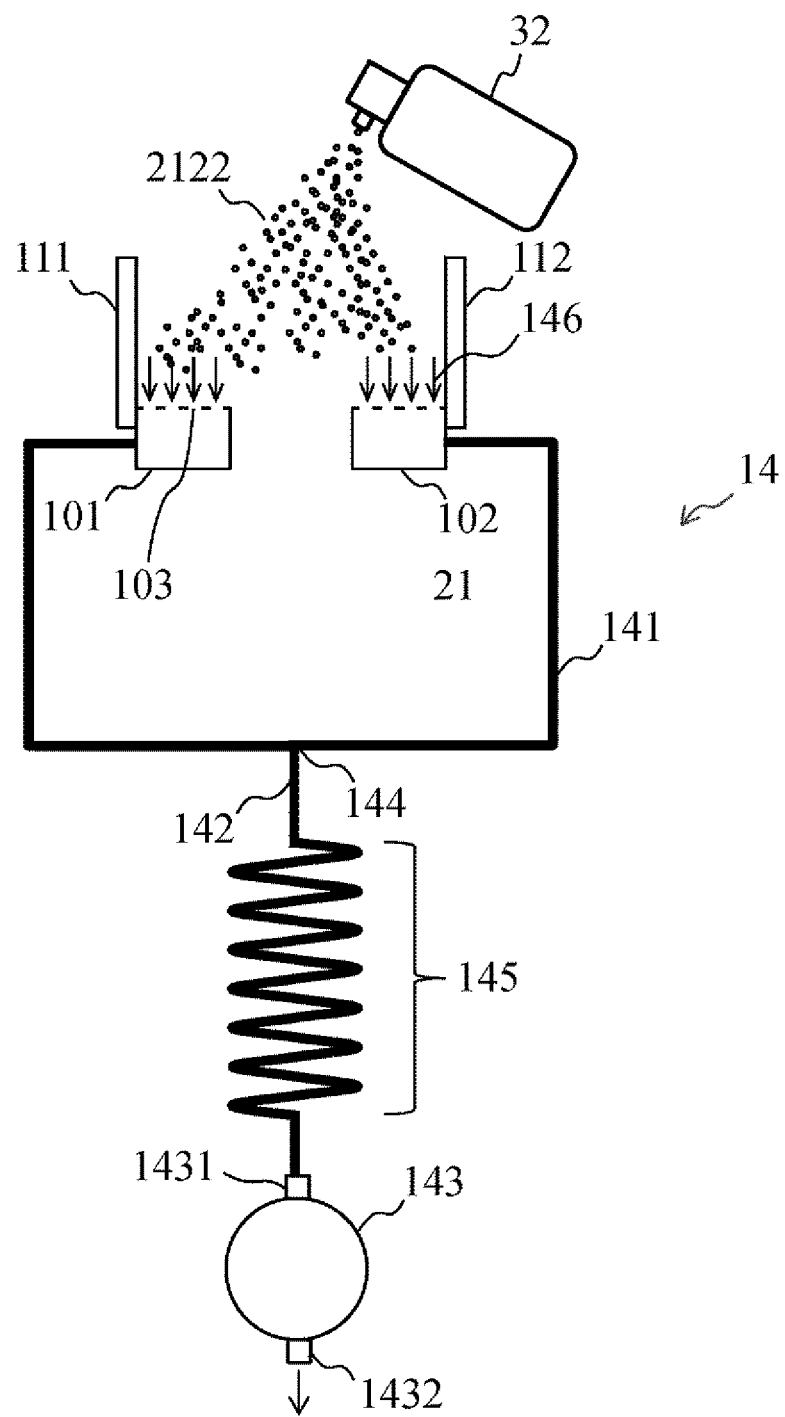
FIG. 12 is a view illustrating a surface treatment method for a coil portion of a sixth example.

Example 3 of the present invention is described in conjunction with FIG. 9. In FIG. 9, a pipe includes multiple coil portions. FIG. 9 exemplifies a case where the number of coil portions is two, but the number may be two or more.

The range of the size of particle to be taken care of by the coil portions is determined according to Formula 6 for determining the target size of particles to be captured, which is a deformation of Formula 4. It is desirable that the shapes of the coil portions are determined such that the size of particles to be captured by the coil portion 1452 on a downstream side is smaller than that to be captured by the coil portion 1451 on an upstream side.

[Math. 6]

$$d = \sqrt{\frac{9\pi\mu D_0 D_1^3}{4\rho Q L_a}} \quad \text{[Formula 6]}$$

As can be seen from Formula 6, the inside diameter D1 of the coil portion makes the greatest contribution to a diameter d of the mist. The smaller the inside diameter the finer mist can be captured. Therefore, it is favorable that, in comparison between the inside diameter of the coil portion 1451 on the upstream side and that of the coil portion 1452 on the downstream side, large mist is captured on the upstream side and small mist is captured by the coil portion 1452 on the downstream side.

The present example has the following effect. In cases where the distribution of target mist sizes covers a wide range or the distribution of mist sizes includes several peaks, when the shape of each coil portion is determined such that large mist is captured by the coil portion 1451 on the upstream side and small mist is captured by the coil portion 1452 on the downstream side, the lengths of the coil portions can be set to the minimum, enabling a reduction in size and cost of the apparatus.

Example 4

Example 4 of the present invention is described in conjunction with FIG. 10. FIG. 10 is a view illustrating a coil portion the inside diameter of which gradually varies from upstream to downstream. FIG. 10 indicates that the inside diameter is reduced uniformly. However, the inside diameter may vary in stages.

The present example has the following effect. In cases where the distribution of target sizes of the mist 212 covers a wide range or the distribution of the sizes of the mist 212 includes several peaks, when the shape of the coil portion 145 is determined such that large mist 212 is captured by an upstream side of the coil portion 145 (a region having a larger inside diameter) and small mist 212 is captured by a downstream side of the coil portion 145 (a region having a smaller inside diameter), the length of the coil portion 145 can be set to the minimum, enabling a reduction in size and cost of the apparatus.

Example 5

Example 5 of the present invention is described in conjunction with FIG. 11. FIG. 11 is a view illustrating a coil portion the inside diameter and the loop diameter of which gradually vary from upstream to downstream. FIG. 11 indicates that the inside diameter and the loop diameter are reduced uniformly. However, the inside diameter and the loop diameter may vary in stages.

The present example has the following effect. In cases where the distribution of target sizes of the mist 212 covers a wide range or the distribution of the sizes of the mist 212 includes several peaks, when the shape of the coil portion 145 is determined such that large mist 212 is captured by an upstream side of the coil portion 145 (a region having larger inside diameter and loop diameter) and small mist 212 is captured by an downstream side of the coil portion 145 (a region having smaller inside diameter and loop diameter), the length of the coil portion 145 can be set to the minimum, enabling a reduction in size and cost of the apparatus.

Example 6

Example 6 of the present invention is described in conjunction with FIG. 12.

The present example facilitates treatment that ensures the capture of mist with the particle suction capture mechanism. As illustrated in FIG. 12, the air intake device 143 is activated, and then treatment mist 2122 obtained as surface treatment liquid is atomized by a treatment mist source 32, e.g., a spray or a nebulizer, is fed to the great number of holes 103, which are present through the upper surfaces of the container gripping mechanisms 101, 102. The surface treatment liquid changes the wettability of the interior surface of the coil portion, provides adhesiveness, or provides a function of preventing growth of fungi or bacteria. The size of the treatment mist 2122 is equal to or more than the smallest size that can be recovered by the coil portion. The treatment mist 2122 passes through the holes 103, reaches the coil portion 145, is captured on the inner wall, and is coated on the inner wall. Furthermore, as illustrated in FIG. 8, the waste liquid collection equipment 1471 and the pipe 1422 may be inserted between the pipe 142 and the air intake device 143 on a downstream side of the coil portion 145 and on an upstream side of the air intake device so that, when the surface treatment liquid is turned into a droplet and flows downward, the droplet does not enter the air intake device 143. Furthermore, the connection between the pipe 142 and the air intake device 143 may be released, and an air intake device for surface treatment may be connected.

The present example has the following effect. Without disassembling the particle suction capture mechanism, the suction function of the particle suction capture mechanism may be used to suck the surface treatment mist 2122 and coat the inside of the pipe. Therefore, the operation is made easier. Furthermore, even when the coating is separated due to maintenance, e.g., cleaning, coating can easily be performed again. Furthermore, because the surface treatment liquid is turned into mist, the mist is adhered to a portion where the sample solution tends to be accumulated, enabling a reduction in amount of the surface treatment liquid and a reduction in processing cost.

REFERENCE SIGNS LIST 1 uncapping device
2 sample container
3 nebulizer
13 uncapping mechanism
14 air intake system
21 sample solution
22 cap
31 cleaning mist source
32 treatment mist source
101 container gripping mechanism (left side)
102 container gripping mechanism (right side)
103 hole
111 partition plate (left side)
112 partition plate (right side)
141 pipe
142 pipe
143 air intake device
144 branch portion
145 coil portion
146 airflow
147 recovery bottle
149 control valve
211 airborne droplet
212 mist
215 droplet
1421 pipe
1422 pipe
1431 air intake port
1432 discharge port
1451 coil portion
1452 coil portion
1471 waste liquid collection equipment
1481 flow rate sensor
1482 temperature and humidity sensor
2121 cleaning mist
2122 treatment mist
2151 waste droplet

The invention claimed is:

1. An uncapping device to remove a cap from an opening of a container by changing a relative distance therebetween, comprising:
a pair of container gripping mechanisms including a pair of half-cylinder partition plates, a pair of half-cylinder inner surfaces configured to grip the container, and a pair of upper surfaces disposed between the partition plates and the inner surfaces, the upper surfaces each including one or more suction holes arranged thereon;
an uncapping mechanism configured to grip and remove the cap from the opening of the container gripped by the pair of container gripping mechanisms;
a first pipe connected to the one or more suction holes;
a coil portion connected to the first pipe and consisting of a helically curved second pipe;
a suction device connected to the first pipe via the coil portion, and configured to suck gas containing a mist through the one or more suction holes, the first pipe and into the coil portion,
wherein the coil portion captures particles of the mist therein, and
wherein the coil portion has a predetermined shape defined by:

$$L_a = \frac{9\pi\mu D_0 D_1^3}{4\rho d^2 Q},$$

where $D_0$ is a loop diameter of the coil portion, $D_1$ is an inside diameter of the coil portion, d is a diameter of the particles of the mist, $\rho$ is a density of the particles, $\mu$ is a viscosity of the gas, Q is a flow rate of the gas, and $L_a$ is a minimum length of the coil portion to capture the particles of the mist.

2. The uncapping device according to claim 1, wherein the coil portion is detachable with respect to the first pipe and the suction device.

3. The uncapping device according to claim 1, wherein the helically curved pipe portion has the inside diameter or the loop diameter that varies between an upstream side connected to the first pipe and a downstream side connected to the suction device.

4. The uncapping device according to claim 3, wherein the helically curved pipe portion is formed such that either the inside diameter or the loop diameter or both on a downstream side connected to the suction device is smaller than that on an upstream side connected to the first pipe.

5. The uncapping device according to claim 1, wherein the helically curved pipe portion has an inner wall surface formed with an irregular shape or provided with a coating that changes a wettability, or increases an adhesiveness or antibacterial property of an inner wall surface.

6. The uncapping device according to claim 1, wherein the helically curved second pipe is transparent.

7. The uncapping device according to claim 1, further comprising:
a drainage container connected to the coil portion and the suction device,
wherein the helically curved pipe portion has one end connected to the pipe and the other end connected to the waste liquid container, and the suction device is connected to the waste liquid container.

8. The uncapping device according to claim 1, wherein the suction device is configured to generate the flow rate of 20 liters/minute or more.

9. A device configured to have gas containing a mist introduced therein and to capture particles of the mist therein, the device consisting of:
a helically curved pipe having a predetermined shape defined by:

$$L_a = \frac{9\pi\mu D_0 D_1^3}{4\rho d^2 Q},$$

where $D_0$ is a loop diameter of the helically curved pipe, $D_1$ is an inside diameter of the helically curved pipe, d is a diameter of the particles of the mist, ρ is a density of the particles, μ is a viscosity of the gas, Q is a flow rate of the gas, and $L_a$ is a minimum length of the coil portion helically curved pipe to capture the particles of the mist.

* * * * *